United States Patent [19]
Larsen

[11] Patent Number: 5,170,666
[45] Date of Patent: Dec. 15, 1992

[54] NONDESTRUCTIVE EVALUATION OF COMPOSITE MATERIALS USING ACOUSTIC EMISSIONS STIMULATED BY ABSORBED MICROWAVE/RADIOFREQUENCY ENERGY

[76] Inventor: Lawrence E. Larsen, 308 Hamilton Ave., Silver Spring, Md. 20901

[21] Appl. No.: 677,565

[22] Filed: Mar. 29, 1991

[51] Int. Cl.$^5$ .................................. G01N 29/12
[52] U.S. Cl. ........................... 73/571; 73/579; 73/655; 73/643
[58] Field of Search ............... 73/584, 587, 579, 588, 73/601, 653, 655, 656, 657, 643, 571

[56] References Cited

U.S. PATENT DOCUMENTS

| | | |
|---|---|---|
| 3,308,463 | 3/1967 | Emerson . |
| 3,946,600 | 3/1976 | Rettig et al. . |
| 4,044,253 | 8/1977 | Crane . |
| 4,255,971 | 3/1981 | Rosencwaig ............ 73/643 |
| 4,385,634 | 5/1983 | Bowen .................. 73/643 |
| 4,484,820 | 11/1984 | Rosencwaig ............ 73/643 |
| 4,513,384 | 4/1985 | Rosencwaig ............ 73/643 |
| 4,523,473 | 6/1985 | Chamuel . |

OTHER PUBLICATIONS

"Generation of Elastic Waves by Transient Surface Heating" by White, R. M., Journal of Applied Physics, vol. 34, No. 12, pp. 3559–3567 (Dec. 1963).

*Primary Examiner*—Hezron E. Williams
*Assistant Examiner*—Rose M. Finley

[57] ABSTRACT

A method and apparatus for nondestructive evaluation of a composite material specimen is characterized by exposing the specimen to pulsed radio frequency energy to produce an elastic wave that propagates on the surface of the specimen. The wave is detected by a piezoelectric or electro-optic displacement mode transducer which produces a signal corresponding to the wave. The signal is analyzed by a processor to classify the specimen into one of a plurality of predetermined reference groups defined in accordance with a minimum number of defective and nondefective samples.

13 Claims, 5 Drawing Sheets

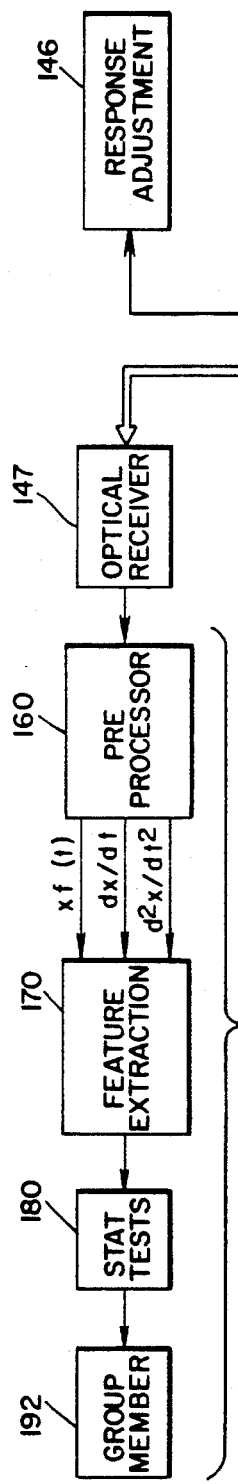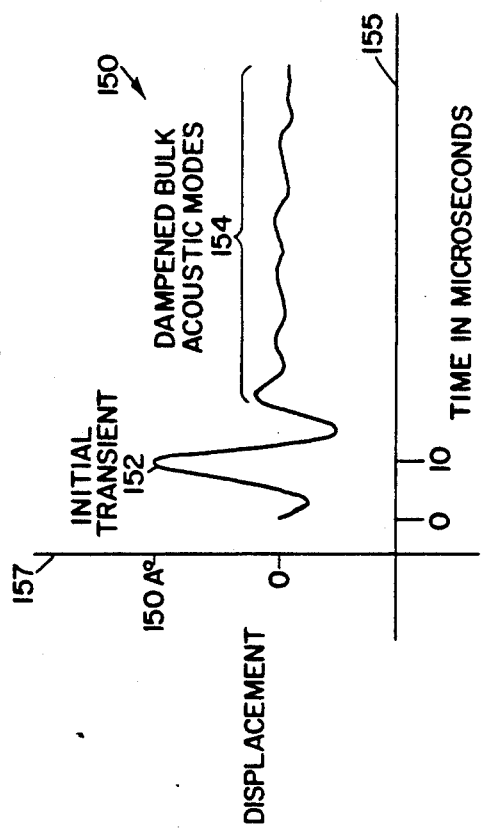
Fig.7
Fig.8

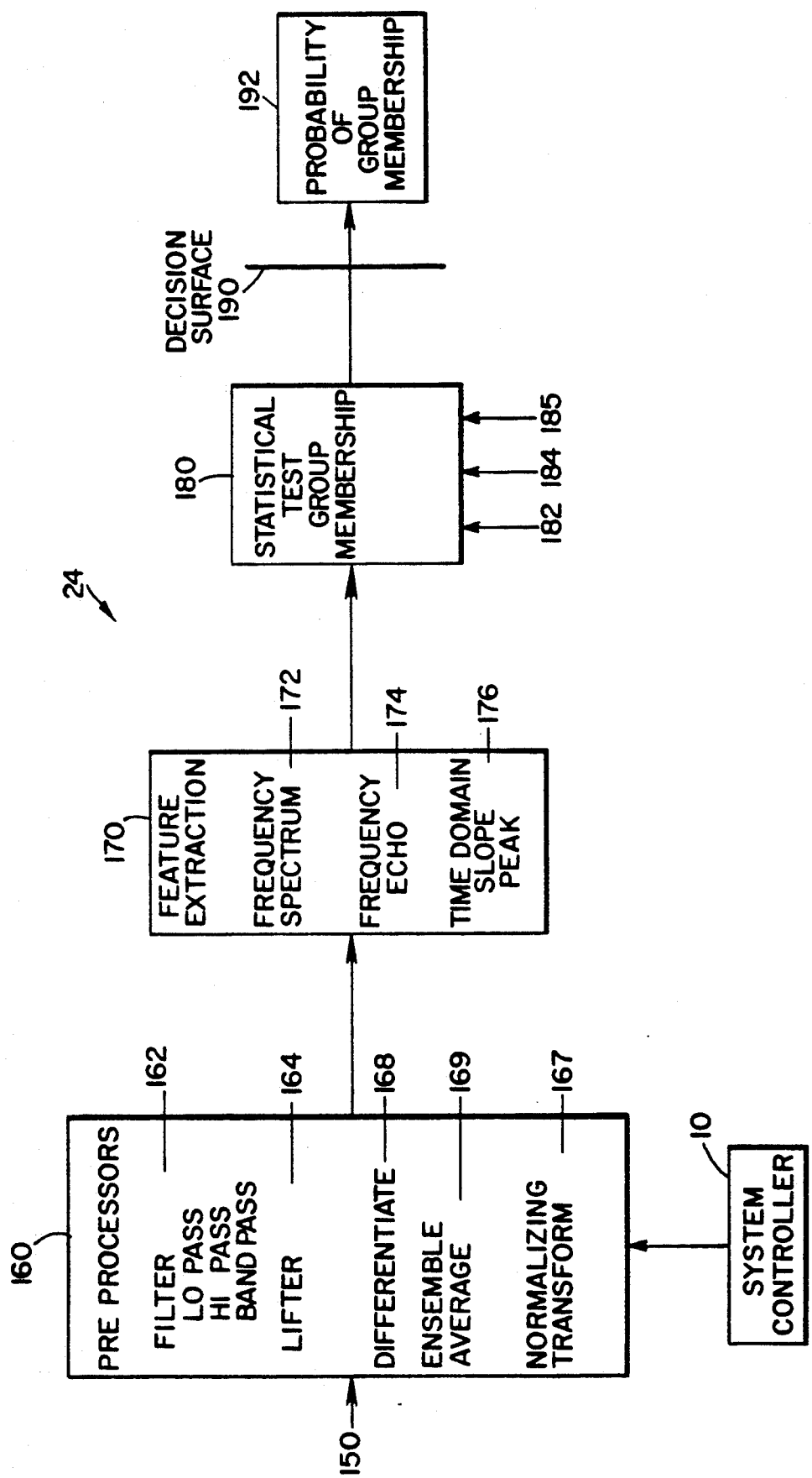

NONDESTRUCTIVE EVALUATION OF COMPOSITE MATERIALS USING ACOUSTIC EMISSIONS STIMULATED BY ABSORBED MICROWAVE/RADIOFREQUENCY ENERGY

This application is based on Disclosure Document No. 223348 filed Mar. 30, 1989.

BACKGROUND OF THE INVENTION

One method for nondestructively evaluating or inspecting mechanical materials, components, systems and the like is through measurement of acoustic energy emitted by a specimen under test when it is placed under loads that simulate what the specimen may be expected to experience in use. The load produces strains in the specimen that are relieved by stress waves produced at early failure sites. These stress waves propagate as surface elastic waves which may be sensed as impulsive "sounds" of broad bandwidth. The acoustic emissions are detected by electroacoustic transducers closely coupled to the specimen.

Another nondestructive evaluation technique is photoacoustic spectroscopy. In this case, a laser pulse is absorbed at the surface of the specimen. The surface is heated and its thermal expansion leads to a surface elastic wave. The instant invention differs by the use of much longer wavelength, by a factor $10^5$ or $10^6$ that permits sub-surface penetration of the composite material specimen. As a result, heat sources are generated in the depth of material and stress is developed over the volume of the specimen, rather than primarily on the surface.

BRIEF DESCRIPTION OF THE PRIOR ART

Generally, acoustic emission has been stimulated by sufficient stress that the specimen under test is deformed up to or beyond its elastic limit such that fractures, delaminations or synthetic plastic flow, for example, occur in the specimen. Recently, acoustic emissions have been detected from chemical stimuli such as corrosion as shown in the U.S. Pat. No. to Rettig et al 3,946,600 and from magnetostrictive stimuli as shown in the U.S. Pat. No. to Chamuel 4,523,473. However, these techniques apply only to metals and paramagnetic materials, respectively.

To date, the nondestructive evaluation of composite materials has not been well-suited for acoustic emission since microscale failures are needed. Furthermore, although the number of acoustic emissions increase as macroscopic failure of the specimen under test is approached, the rate of acoustic emission can either increase or decrease at failure. Thus, the term "nondestructive" must be used with qualification in composite materials that have been at or near the actual destruction of the sample by the mechanical loads needed to stimulate the acoustic emission.

Furthermore, the prior methods, whether mechanical, chemical or magnetostrictive, are insensitive to dielectric and thermal properties of the composite material that may be important for its ultimate use. For example, carbon carbon-fiber materials serve not only structural roles in airplane frames, but also a role in suppression of electromagnetic interference effects that depend upon their complex permittivity. Similarly, carbon fiber composites used in orthopedic implants from joint prosthetics must meet not only mechanical but also bioelectric properties for osteocyte and fibroblast ingrowth.

Both industrial and medical applications for composite materials often involve adhesive bonding. In the case of industrial applications, these bonds may be to another composite, to plastic or to metal. In the case of orthopedic implants, bonds to bone with polymethylmethacrylic cements are an important consideration in the durability of join replacement. The present invention is applicable to testing such bonds as well as the materials. Prior methods use acoustic emission for bond testing by mechanical stress as disclosed in the U.S. Pat. No. to Crane 4,044,253. The present invention differs in that elastic surface waves are stimulation by impulsive thermal expansion from heat sources induced by the absorption of high energy pulses of microwave or radio frequency energy by the specimen under test.

SUMMARY OF THE INVENTION

Accordingly, it is a primary object of the present invention to provide a method and apparatus for nondestructive evaluation of a composite material specimen including a transmitter for generating pulsed radio frequency energy and transmitting the energy to the specimen in order to produce an elastic wave that propagates on at least a surface of the specimen. The elastic wave is detected by a detector connected with the specimen surface. The detector generates a signal corresponding with the elastic wave. A signal processor is connected with the detector for analyzing the signal in order to classify the specimen into one of a plurality of predetermined reference groups defined in accordance with a minimum number of defective and non-defective samples.

The transmitter preferably has an adjustable duty factor for inducing heat in the specimen to determine the temperature coefficient of transduction.

The apparatus also includes a support for the specimen which isolates the specimen from vibrations from sources other than the radio frequency energy source during travelling or standing wave RF exposure.

According to a more specific embodiment of the invention, the signal processor extracts features from the signal and from the reference groups by time domain, frequency domain, or frequency domain (i.e., log frequency vs. log magnitude) analysis order to provide loci in a multivariate space for the reference groups and for the specimen. More particularly, the processor defines boundaries in accordance with the loci to separate the reference groups. The locus of the specimen falls within one of the boundaries, thus classifying the specimen in one of the groups.

BRIEF DESCRIPTION OF THE FIGURES

Other objects and advantages of the invention will become apparent from a study of the following specification when viewed in the light of the accompanying drawing, in which:

FIG. 7 is an illustration of an electro-optical transducer for detecting surface elastic waves in the specimen according to an alternate embodiment of the invention;

FIG. 8 is a graphical representation of the signal output from the transducer of either FIGS. 6 or 7 representing surface elastic wave; and FIG. 9 is a block diagram of the signal processor of the apparatus of FIG. 1.

DETAILED DESCRIPTION

Figure 1:
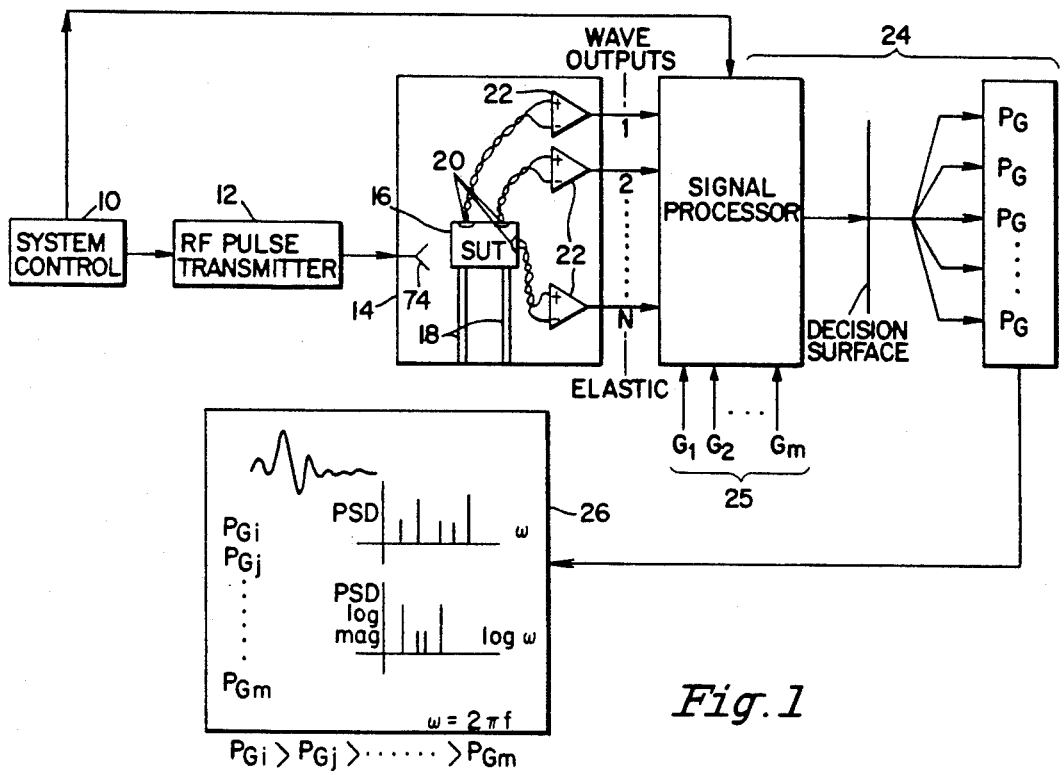
FIG. 1 is a block diagram of the nondestructive specimen evaluation apparatus according to the invention.

The apparatus for nondestructive evaluation of composite materials using acoustic emissions stimulation by absorbed microwave/radiofrequency energy will first be described with reference to FIG. 1.

A system controller 10 is connected with a radio frequency (RF) pulse transmitter 12 which supplies pulses of microwave/radiofrequency energy to an exposure assembly 14 to couple the energy pulses into a specimen 16 being tested or evaluated. The specimen 16 rests on vibration isolation supports 18 and has one or more detectors 20 mounted on the surface thereof. As will be developed below, when the energy pulses are coupled into the specimen, an elastic wave is propagated on the specimen surface. The detectors 20 detect the elastic wave and generate a signal in response thereto. Signal conditioners such as amplifiers 22 are connected with the detectors to enhance the signals for delivery to a signal processor 24. Under control of the system control 10, the signal processor analyzes the signals corresponding with the elastic wave in order to classify the specimen into one of a plurality of predetermined reference groups. A display 26 is connected with the processor for indicating the test results and the statistical decision for group membership of each specimen under test in terms of the probability P of correct classification of groups G.

Figure 2:
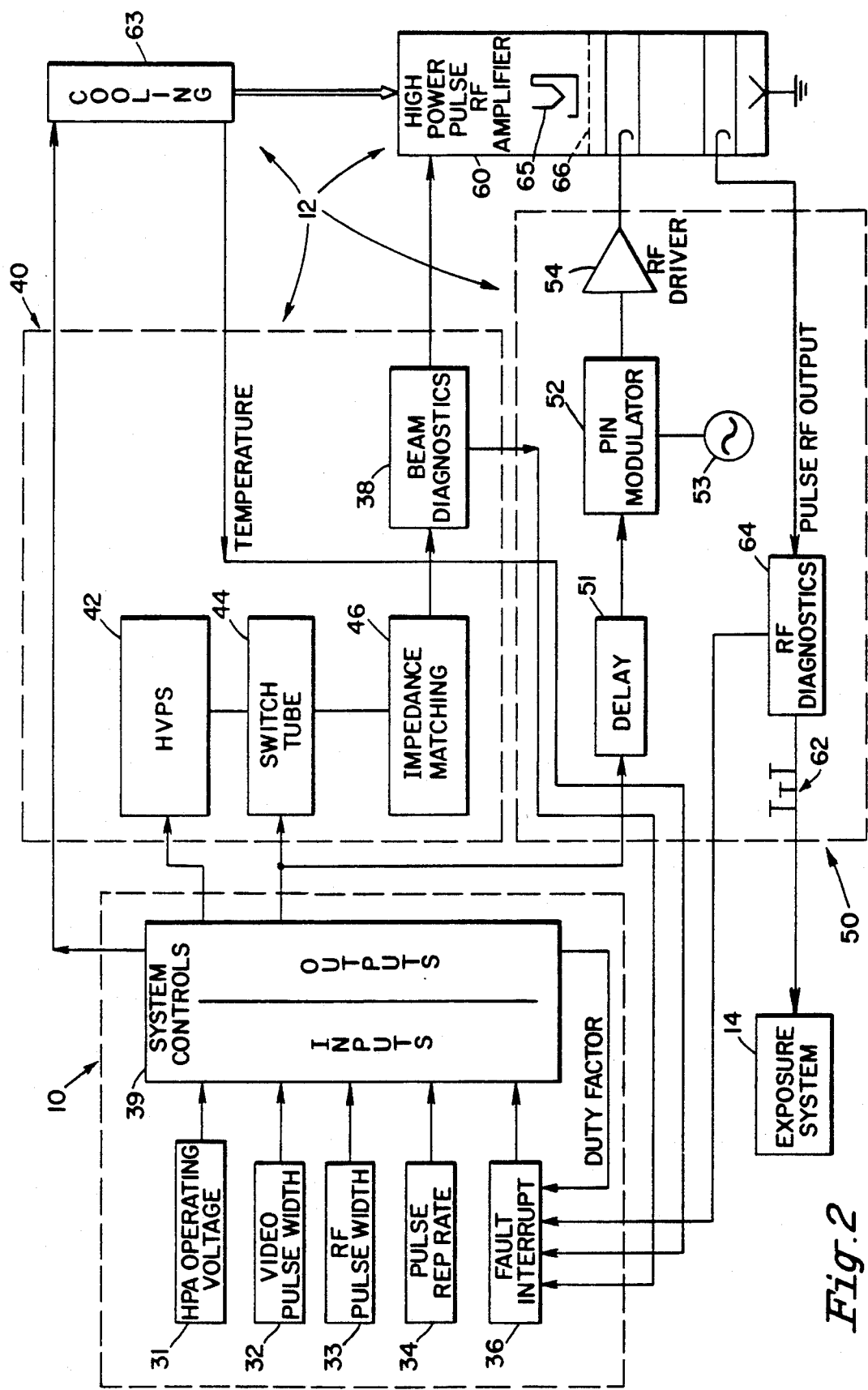
FIG. 2 is a block diagram of the transmitter of the apparatus of FIG. 1.

Referring now to FIG. 2, the transmitter 12 of the invention will now be described. The transmitter is similar to a radar transmitter. An electron beam modulator applies high voltage pulses to an RF output device such as a power oscillator or a power amplifier. Either converts the kinetic energy of the electron beam into RF/microwave power. The preferred embodiment comprises an RF high power amplifier since this allows better control of the envelope of the RF pulse coupled into the specimen under test.

The transmitter interfaces to a system controller 10, a video chain 40 and an RF chain 50 that converge at a high power amplifier 60. The controller 10 is connected with inputs for desired modulator voltage 31, video (i.e. electron beam) pulse width 32, RF pulse width (which must be less than video pulse width) 33, the pulse repetition rate 34, and beam diagnostic sensors (beam voltage and current) 38, via a fault interrupt 36 and data interface 39. The video chain is composed of a high voltage power supply 42, connected with a switch 44, under control of controller 10 via interface 39, and impedance transformer 46, connected with a high power amplifier 60 via beam diagnostic sensor 38.

The preferred embodiment of the modulator uses a hard-vacuum power triode as switch 44 and pulse transformer 46 connected to the high power amplifier cathode 55. This allows nearly continuous adjustment of pulse width at lower impedances than that of the high power amplifier. Line modulators may be substituted if this flexibility is not desired. The beam modulator may also be embodied as pulses to a control structure 56 of the high power amplifier as this allows faster RF pulse rise times. The control structure may be a modulating anode in a magnetically focused klystron or a control grid in an electrostatically focused klystron. In this case, the high voltage power supply 42 is connected with cathode 55 and the system control 39 video pulse output is applied to the control structure 56.

The RF chain 50 begins with a low power RF oscillator 53. Low power pulses are produced by a PIN modulator 52, the output of which serves a input to the RF driver amplifier 54 connected with the RF input of the high power amplifier 60. The onset of the RF pulses at the amplifier are delayed 51 from the onset of the video pulse. Further, the RF pulse is of shorter width than the video pulse. The RF pulse is nestled within the video pulse to maximize beam efficiency. Also connected with the high power amplifier are a tuning device 62, and RF diagnostics apparatus 64, connected with the fault interrupt 36.

The high power amplifier preferably comprises a klystron in the decimetric and centimetric regions of the spectrum. The advantages are high beam efficiency in order to reduce beam input power requirements and long pulse width for a given RF output power to obtain the energy per pulse needed to produce easily detectable elastic waves in the target. Other long pulse high power amplifiers may be substituted for the multi-cavity klystron depending upon the carrier frequency. At VHF and UHF frequencies, a coaxial tetrode may be advantageous. At frequencies in the millimeter wave region, an extended interaction oscillator/amplifier may be advantageous. The high power amplifier is preferably one with a thermionic cathode to support long RF pulse widths in order to allow high energy per pulse and, therefore, high strain in the target.

Figure 3:
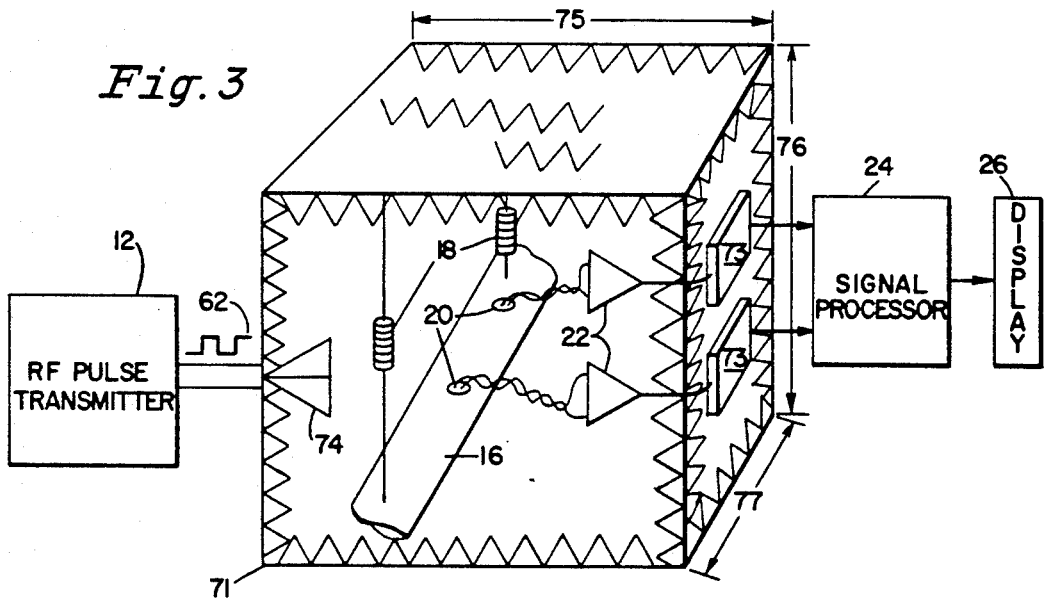
FIG. 3 is an illustration of a travelling wave exposure system of the apparatus of FIG. 1.

Referring now to FIG. 3, there is illustrated the travelling wave method for exposure of the specimen under test. The specimen 16 is illuminated by a high power RF pulse, or series of pulses, in the far field of an antenna 74 in free space or an anechoic chamber 71 with absorber material 78 to suppress scattered fields that would otherwise also illuminate the specimen. The antenna 74, the dimensions 75, 76, 77 of the chamber and the length of the absorber 78 are selected to achieve uniform illumination of the specimen 16 according to methods well known to those skilled in the art. The surface elastic wave sensors or detectors 20 are connected with differential signal conditioning amplifiers 22 the outputs of which penetrate the chamber walls via low pass filter networks 73 that pass the response while the RF is rejected to prevent leakage.

Signal conditioning may be either inside or outside of the chamber, but electromagnetic interference must be minimized if the amplifier is inside the chamber by methods such as shielding and bypassing as is well known to those skilled in the art. Although an anechoic chamber is more expensive than a standing wave chamber (FIG. 4), it has the advantage that exposure geometry is well controlled. A terminated transmission line is an alternative traveling wave exposure system, but this will increase the wavelength in comparison to the free space wavelength at the same carrier frequency.

Figure 4:
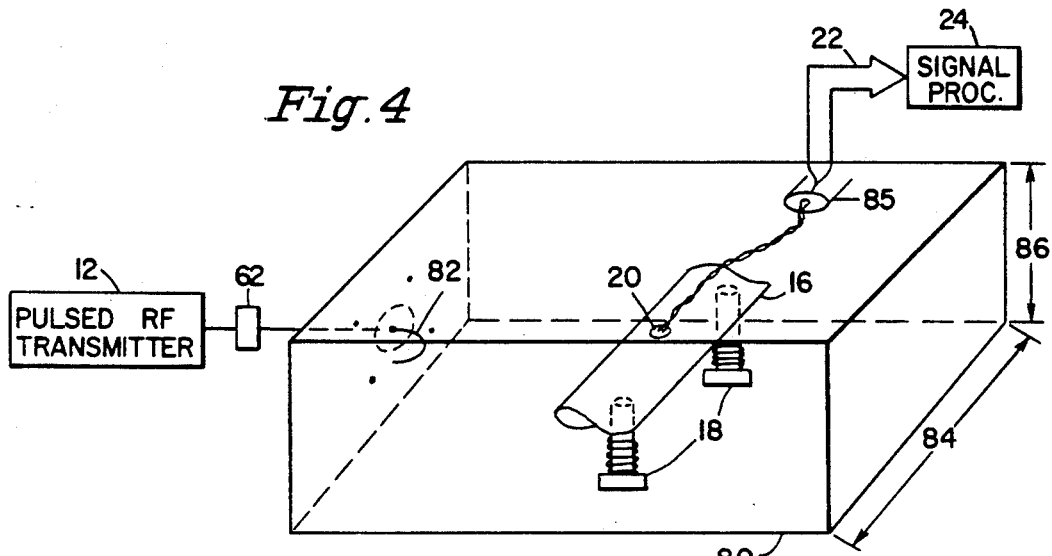
FIG. 4 is an illustration of a standing wave exposure system of the apparatus of FIG. 1.

FIG. 4 illustrates the illumination of the specimen 16 in a standing wave chamber 80 of reflective walls having dimensions 84 and 86 that support dominant mode propagation of the pulse modulated RF/microwave carrier frequency produced by transmitter 12. A loop feed 82 is shown to couple the RF pulse into the chamber, but an electric field feed may be substituted. Impedance matching 62 between the transmitter 12 and the standing wave exposure chamber 80 will generally be needed to optimize power transfer into the specimen 16. The elastic wave detector 20 is coupled to the conditioning amplifier 22 the output from which penetrates the chamber walls via a waveguide below cutoff port 85 advantageously cross-polarized to the direction of the electric field.

Figure 5:
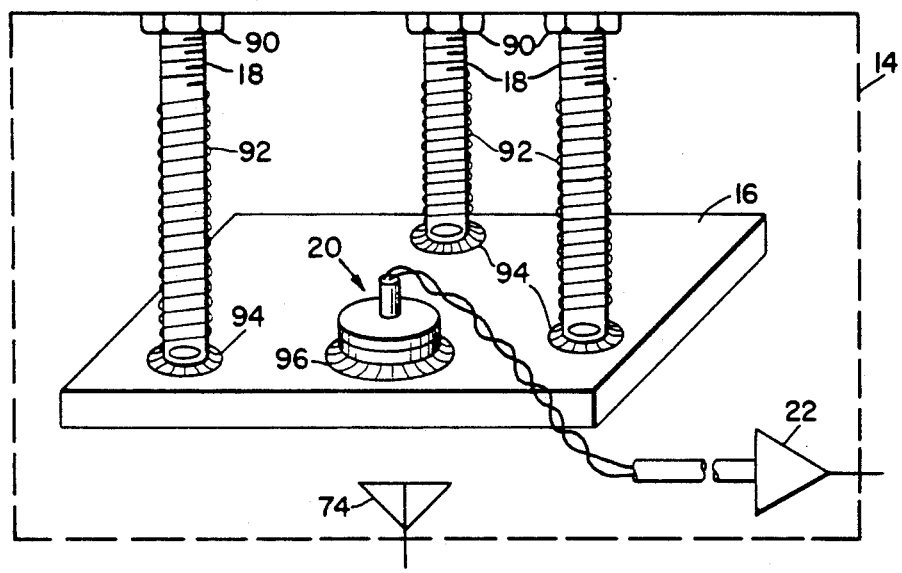
FIG. 5 is an illustration of a specimen vibration isolation mechanism.

FIG. 5 is a diagrammatic representation of the support 18 for the specimen 16 in an exposure system 14 such that the specimen is isolated from sources of vibration via compliant elastomeric supports 92 attached to the specimen by an adhesive 94. The supports 18 are threaded and leveled by adjustment nuts 90 connected therewith. Close coupling of the detector 20 to the surface of the specimen under test 16 is accomplished by thin adhesive 96. Detector 20 responds to displacement of the surface of the specimen or the first and/or second derivative of the displacement with respect to time, as a stress wave propagates in the specimen as result of strain induced by absorption of the RF pulse. Detectors that respond to displacement include electro-optic types with later calculation of the velocity and acceleration. Piezoelectric types respond to acceleration. Electromagnetic types (i.e. variable reluctance) respond to velocity.

Figure 6:
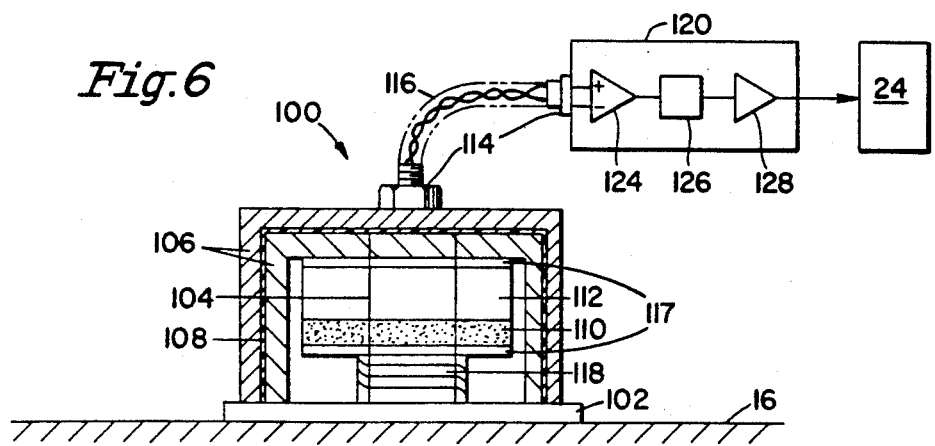
FIG. 6 is a detailed sectional view of a piezoelectric transducer for detecting surface elastic waves in the specimen.

FIG. 6 illustrates a sensor or detector 100 based on piezoelectric transduction in the compression mode. This sensor is sensitive to acceleration of the surface. It is composed of a base plate 102, a central support pillar 104, a shield/housing 106, constrained layer dampening material 108, an insulated disk of piezoelectric material 110 with mass loading 112, and a shielded pair of wires interfaced to signal conditioner 120 via twinax connector 114 and cable 116 with a disk 117 to adjust the force form spring 118. The signal conditioner 120 preferably implements differential charge amplification 124 and band limiting via a band pass filter 126 prior to a line driver 128. The sensor/conditioner is calibrated in terms of picoCoulombs/meter sec$^{-2}$ by the use of calibrated mechanical acceleration as is known in the art.

There is shown in FIG. 7 an optical sensor 130 that is sensitive to displacement of the specimen surface. Calculation of the first and second derivatives of displacement with respect to time, i.e. velocity and acceleration, is performed by the processor 24. The optical sensor cavity 134 of length 135 with facets 137 on the end walls, one of which is spaced by a gap 140 from a reflective pellicle 136 attached to the surface of the sample 16. A pellicle is not needed if the surface is sufficiently reflective to accomplish the response adjustment described below. The gap 140 must be a small fraction of the cavity length 135. A large area photo detector 138 and a signal conditioning amplifier 143 with photenic transmitter 139 are coupled via optic fiber cable 141 to optic fiber link receiver 147.

The distance 140 between the distal end of the laser cavity 134 and the pellicle 136 is adjusted by piezoelectric cylinder 142 decoupled from the housing 144 by constrained dampening material 145. The response adjustment 146 biases the system in a region where changes in reflectance from the pellicle are linearly related to distance. Other inter-ferometer arrangements are possible, but the external cavity method has the advantage of more compact dimen-sions, point sensing, and sufficient sensitivity (ca. $10^{-7}$ radian or about $10^{-5}$ nanometer for typical laser diodes). Photonic detection has greater bandwidth and improved immunity to radio frequency interference.

FIG. 8 illustrates a typical output indication 150 showing the two major components of the response in terms of displacement as a function of time. These are the initial transient 152 and the dampened acoustic modes 154. The displacement scale 157, with water dominated dielectrics for energy densities in the order of milli- Joules/cm$^2$, is in the order of $10^2$ Angstrom units. The time scale 155 is comparable to the RF pulse timing, in this case a 10 microsec pulse width. The output response 150 may extend in time beyond the end of the RF pulse depending on the Q of structure.

FIG. 9 illustrates a menu of signal processing methods for the response. These are of several broad types: pre-processors 160, feature extraction 170, and statistical tests for group differences 180 with decision algorithms for classification of samples. The tests for group differences compare the response 150 of a specimen under test with samples from reference groups, 182, 183..., tested in the same way to comprise a training set. Known group memberships are used to generate a decision surface 190 for statistical determination of group membership 192 for samples whose membership is unknown according to the principles of learning machines. In this way, the unknown sample is classified in terms of one of the reference groups such as 182 or 184. For a complete discussion of pattern recognition using signal processing to classify specimens, see Nilsson, N.J., *Learning Machines: A Foundation of Trainable Pattern Classifying Systems*, section 1.7 (McGraw-Hill, 1966) which is incorporated herein by reference.

The preprocessor 160 is composed of filters 162 operating in the frequency domain or lifters 164 operating in the quefrency (log frequency, log magnitude) domain and differentiators 168 for displacement data. In addition, normalizing transformation 167 for later parametric tests of groups differences; and ensemble averaging 169 for improved signal to noise ratio are implemented in the preprocessor.

The feature extraction section 170 comprises three categories: frequency domain power spectrum density analysis 172, quefrency domain echo analysis 174, and time domain analysis 176 for slopes and peaks. These features become the parameter space for statistical tests of group membership by 180. These statistical tests are based on reference specimens that represent two or more groups 182 and 184 (for example, pass and fail for matrix voids) for which a decision surface 190 is generated by Bayesian rules against which new specimens are sorted into one of the groups 182, 184, etc., for example.

OPERATION

Specific operational parameters depend upon the specimen to be tested. Pertinent specimen parameters are dimensions, complex permittivity, volume coefficient of thermal expansion, specific heat, thermal conductivity, and density. Pertinent transmitter parameters are carrier frequency, pulse repetition rate, RF pulse rise time, and especially the transmitted energy per RF pulse. The first and last of these in combination determine the spatial distribution and magnitude of induced heat sources. These directly determine the strain placed on the specimen via the intermediates of thermal expansion and thermal conduction for a given spatial distribution of dielectric properties.

In the context of structurally useful composite materials of typical form factors (beams, rods, plates, etc.), the UHF through the S band region of the spectrum offers the greatest utility. The general choice of carrier frequency is determined by the propagation loss of the specimen, the dimensions of the specimen relative to the wavelength of the incident electromagnetic wave, and exposure system construction. As a general rule, high dielectric loss composites, such as carbon carbon-fiber, of thickness typical for structures (in the order of centimeters) that use such material, e.g. brake disks for air craft, will require carrier frequencies in the range of 500 to 1000 MHz. Water dominated dielectrics, such as shown in FIG. 8, will also be most effectively tested with carrier frequencies in that range. Thinner (in the order of millimeters) or lower loss specimens, such as glass reinforced plastic, can be usefully tested with higher carrier frequencies in the range of 1 to 10 GHz. Very thin or very low loss materials such as ceramics can be tested with carrier frequencies in the centimetric range or higher, into millimeter wave frequencies, nominally 10 to 100 GHz.

The peak power used for testing is determined by dielectric breakdown in the specimen or sparking in the exposure system. Breakdown power densities are well-known for various transmission lines and media that may be used in the system. Dielectric breakdown in the specimen is often a fundamental physical limit of the specimen materials and geometry, however. As a rule, peak power densities on the specimen will be well below the 1 Megawatt/cm$^2$ breakdown of air at the pulse widths used for this purpose.

The product of peak power and pulse width determine the energy per pulse. In the case of typical composite materials, the minimum fuse energy sensities needed to produce easily detectable acoustic emission range from 1 to 10 milli-Joules/cm$^2$. In lossy targets, the peak pressures so produced are in the order of tens of Kilo- Pascals, and the peak pressure has been observed to scale with the energy per pulse. Pressure rise times are comparable to rise time of the RF pulse. The peak power of the preferred embodiment is in the range 10 to 100 KW. The pulse widths range from 10 to 100 microsec leading to pulse energies of 0.1 to 10 Joules.

The pulse repetition rate is pertinent from three perspectives. First, the total number of pulses used by the data acquisition system reduce the influence of random noise in proportion to the square root of the number of pulses. Thus, the data acquisition period for a specified signal to noise ratio depends upon the pulse repetition rate. Second, the pulse repetition rate in combination with the energy per pulse determines the average power absorbed by the target. This allows parametric study of the temperature of the target for temperature coefficient of the elastic wave transduction. It has been observed that in the case of viscoelastic solids, the temperature coefficient is positive. Third, the pulse repetition rate may be used in a burst mode to stimulate macroscopic acoustic resonances in the target.

It is undesirable to induce surface elastic waves in the elastomeric supports for the target. The choice of materials for these vibration isolators is driven by low microwave loss, hence low heating, and high mechanical dampening. Low loss polymeric materials with high internal dampening such as artificial rubber are preferred.

The reference groups are selected to include the defects that may be expected in the specimen. These represent, at a minimum, those defects related to manufacturing and/or installation as well as those produced by service use of the specimen. Examples of the former include voids in the matrix while fiber/matrix delamination may be either a manufacture defect or a service defect.

The reference groups train a pattern classifier to implement a decision surface that minimizes the probability of misclassification subject to a cost weighing in the Bayesian mode. The specimens are tested by the same decision surface so generated and must be classified into one of the training sets.

Once the operational parameters have been determined according to the methods described above, the transmitter 12 is configured to produce the desired carrier frequency, energy per pulse, pulse rise time, and pulse repetition rate. An exposure system 14 is selected as appropriate for the samples. The pulse repetition rate is used for ensemble averaging of the response 150 recorded first from the reference groups and then from the specimen.

The samples are placed in vibration isolated support of the exposure system and the elastic wave transducer is attached to the surface of the sample. The samples are exposed to the RF pulses and responses are recorded for use by the statistical processor 180. The decision surface is generated.

The specimens 16 are tested in the same exposure system and with the same elastic wave transducers and by the same transmitter operational parameters as the reference groups. The responses 150 of the specimens are subjected to the same preprocessing (e.g. averaging) and feature extraction (e.g. peaks of the initial transient and subsequent acoustic modes) as the samples of the reference groups. Specifically, the bank pass, gain, and ensemble averaging are performed in the same way for all members of a given group. The specimens are then classified by decision surface 190 into one of the reference groups. The display includes the response, the features extracted and the probability of group membership for the specimens into each of the reference groups. Group membership is determined by the highest probability of correct classification. Generalized distance of the unknown sample from the reference group centroids, in combination with the distributional statistics of the reference group samples, produce the decision surface. This is most often a hyper-plane.

While in accordance with the provisions of the patent statutes the preferred forms and embodiments of the invention have been illustrated and described, it will be apparent to those of ordinary skill in the art that various changes and modifications may be made without deviating from the inventive concepts set forth above.

What is claimed is:

1. Apparatus for microwave nondestructive evaluation of specimen comprising:
    (a) microwave means comprised of
        (1) generating means to generate, at least one microwave pulse of predetermined pulse energy, carrier frequency, and polarization; and
        (2) directing means to direct said microwave pulse to a microwave coupling means, said coupling means comprising a chamber and a microwave transition into said chamber, said chamber enclosing said specimen; and (b) receiving means to detect elastic waves which appear on at least one surface of said specimen wherein said receiving means responds to strain in said specimen from impulsive stress imposed on said specimen by absorbtion of said microwave pulse;

(c) measuring means to read output signals from said generating and receiving means, said measuring means evaluating said output signals corresponding to surface displacement as a function of time;

(d) processing means acting upon said measuring means output signals, said processing means classifying said specimens as members of one of at least two reference groups, said reference groups being predefined by prior tests upon known samples.

2. Apparatus as defined in claim 1, wherein
(a) said generating means is comprised of a high power, pulse microwave source with at lest two duty factors, one of higher average power for bulk heating of the specimen and one a low duty factor, to evaluate said specimen with at least one microwave pulse; and wherein
(b) said directing means is comprised of at least one microwave transmission line that operantly connects the output of said generating means to said microwave coupling means.

3. Apparatus as defined in claim 1, with said microwave transition energizing said chamber enclosing said specimen to transfer said microwave pulse of said preselected carrier frequency, pulse energy, and polarization from said generating means into said specimen via a microwave traveling wave.

4. Apparatus as defined in claim 1, with said microwave transition energizing said chamber enclosing said specimen to transfer said microwave pulse of said preselected carrier frequency, pulse energy, and polarization from said generating means into said specimen via a microwave standing wave.

5. Apparatus recited in claim 1, said receiving means comprising at least one broad bandwidth piezoelectric transducer attached to at least one surface of said specimen thereby responding to surface acceleration from absorbtion of said microwave pulse by said specimen.

6. Apparatus recited in claim 1, said receiving means comprising at least one broad bandwidth electro-optic transducer responding to displacement of at least one surface of said specimen from absorbtion of said microwave pulse.

7. Apparatus in claim 1 wherein said measuring means comprise signal conditioning for said receiving means, and interfacing said received signals to said processing means rejecting electromagnetic interference.

8. Apparatus as in claim 3, wherein said chamber is a microwave anechoic enclosure containing said specimen and said microwave transition thereby transferring said microwave pulse into said specimen by microwave plane waves wherein said traveling wave has wavelength substantially equal to the free space wavelength of said carrier frequency.

9. Apparatus as in claim 3, wherein said chamber is a dominant mode microwave transmission on line terminated in the characteristic impedance of said transmission line containing said specimen and said microwave transition thereby transferring said microwave pulse into said specimen by microwave traveling waves of wavelength greater than the free space wavelength of said carrier frequency.

10. Apparatus as in claim 4 wherein said chamber is a short circuited dominant mode microwave transmission line containing said specimen and said microwave transition thereby transferring said microwave pulse into said specimen by microwave standing waves of wavelength greater than the free space wavelength of said carrier frequency.

11. Apparatus as in claim 1 wherein
(a) said directing means provides adjustable tuning to match said specimen and enclosure to said generating means; and
(b) said specimen is isolated from sources of mechanical vibration other than those induced in said specimen by absorbtion of said microwave pulse.

12. Apparatus as in claim 1, wherein said processing means is a trainable pattern recognition apparatus comprised of a decision boundary in a multivariate space defined by extracting time and frequency domain features from said received signals from said reference group members constituted of specimens known to be, at a minimum, normal or defecting reference specimens to classify by said decision boundary unknown specimens as a member of one of said reference groups.

13. A method of nondestructive evaluation comprising the steps of:
(a) Selecting carrier frequency and pulse parameters to induce heat sources in a specimen under evaluation by absorbtion of at least one microwave pulse;
(b) Supporting said specimen in an exposure chamber that encloses said specimen with isolation from external sources of mechanical vibration;
(c) Generating, directing, and coupling said microwave pulse into said specimen in said exposure chamber;
(d) Receiving surface elastic waves secondary to absorbtion of said microwave pulse;
(e) Measuring at least one of surface displacement, surface velocity, or surface acceleration as a function of time following absorbtion of at least one microwave pulse;
(f) Processing data generated during said measuring step to classify each specimen by time and frequency domain features extracted from said time function whereby said specimen is identified as a member of one of at least two predetermined reference groups, said reference groups being previously defined by applying steps a through e with controlled pulse parameters and exposure chamber conditions to specimens known to be members of, at a minimum, normal or defective groups.

* * * * *